(12) United States Patent
Li et al.

(10) Patent No.: US 9,364,309 B2
(45) Date of Patent: Jun. 14, 2016

(54) POROUS SURGICAL FILMS

(71) Applicant: Boston Scientific Scimed Inc., Maple Grove, MN (US)

(72) Inventors: Jianmin Li, Lexington, MA (US); James Goddard, Pepperell, MA (US); Timothy P. Harrah, Cambridge, MA (US); Doreen Rao, Sudbury, MA (US); Alfred Intoccia, Nashua, NH (US); Leo James Lichte, Riverside, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 268 days.

(21) Appl. No.: 13/762,218

(22) Filed: Feb. 7, 2013

(65) Prior Publication Data

US 2013/0204078 A1 Aug. 8, 2013

Related U.S. Application Data

(60) Provisional application No. 61/596,312, filed on Feb. 8, 2012.

(51) Int. Cl.
*A61F 2/00* (2006.01)
*A61L 31/04* (2006.01)
*A61L 31/14* (2006.01)

(52) U.S. Cl.
CPC ............. *A61F 2/0063* (2013.01); *A61F 2/0045* (2013.01); *A61L 31/04* (2013.01); *A61L 31/146* (2013.01); *A61L 31/148* (2013.01); *A61F 2210/0004* (2013.01); *A61F 2250/0031* (2013.01); *A61F 2250/0067* (2013.01)

(58) Field of Classification Search
CPC ... A61F 2/0036; A61F 2/0004; A61F 2/0031; A61F 2/0045; A61F 2/0063
USPC .......................... 600/29–32, 37; 128/DIG. 25
See application file for complete search history.

(56) References Cited

U.S. PATENT DOCUMENTS

| | | | |
|---|---|---|---|
| 6,031,148 A * | 2/2000 | Hayes et al. | 623/11.11 |
| 8,170,686 B2 * | 5/2012 | Moreci et al. | 607/101 |
| 2006/0122683 A1 | 6/2006 | Stinson | |
| 2008/0221386 A1 * | 9/2008 | Gellman et al. | 600/37 |
| 2009/0069904 A1 | 3/2009 | Picha | |
| 2009/0171143 A1 | 7/2009 | Chu et al. | |
| 2009/0171377 A1 | 7/2009 | Intoccia et al. | |
| 2009/0281558 A1 | 11/2009 | Li | |
| 2009/0281635 A1 | 11/2009 | Li et al. | |
| 2010/0076255 A1 * | 3/2010 | Robertson et al. | 600/30 |
| 2011/0184228 A1 | 7/2011 | Sherry et al. | |
| 2012/0179175 A1 * | 7/2012 | Hammell | 606/151 |

FOREIGN PATENT DOCUMENTS

| WO | 2010/052584 A2 | 5/2010 |
|---|---|---|
| WO | 2010/093333 A1 | 8/2010 |
| WO | 2010/129641 A1 | 11/2010 |

* cited by examiner

*Primary Examiner* — John Lacyk (57) ABSTRACT

According to an aspect of the present invention, surgical films for soft tissue repair are provided. The surgical films comprise at least one sheet of a non-filamentous material within which pores are formed. Further aspects of the invention, among others, pertain to methods of using such surgical films and to kits containing such surgical films.

17 Claims, 3 Drawing Sheets

POROUS SURGICAL FILMS

STATEMENT OF RELATED APPLICATION

This application claims the benefit of U.S. Ser. No. 61/596,312, filed Feb. 8, 2012 and entitled: POROUS SURGICAL FILMS," which is hereby incorporated by reference in its entirety.

FIELD OF THE INVENTION

The present invention relates generally to medical articles, and more particularly to films for surgical applications.

BACKGROUND OF THE INVENTION

Pelvic floor (pelvic support) disorders involve a dropping down (prolapse) of the bladder, rectum, vagina or uterus caused by weakness of or injury to the ligaments, connective tissue, and muscles of the pelvis. The different types of pelvic floor disorders are named according to the organ affected. For example, a rectocele develops when the rectum drops down and protrudes into the back wall of the vagina. An enterocele develops when the small intestine and the lining of the abdominal cavity (peritoneum) bulge downward between the uterus and the rectum or, if the uterus has been removed, between the bladder and the rectum. A cystocele develops when the bladder drops down and protrudes into the front wall of the vagina. In prolapse of the uterus (procidentia), the uterus drops down into the vagina. See, e.g., The Merck Manuals Online Medical Library, Home Edition, "Pelvic Floor Disorders." Pelvic floor disorders are commonly treated by implanting a surgical mesh within the patient's pelvis to support the organ or organs that require support.

Urinary incontinence affects millions of men and women of all ages in the United States. Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results. A popular treatment of SUI is via the use of a surgical mesh, commonly referred to as a sling, which is permanently placed under a patient's bladder neck or mid-urethra to provide a urethral platform. Placement of the sling limits the endopelvic fascia drop, while providing compression to the urethral sphincter to improve coaptation. Further information regarding sling procedures may be found, for example, in the following: Fred E. Govier et al., "Pubovaginal slings: a review of the technical variables," Curr. Opin. Urol. 11:405-410, 2001, John Klutke and Carl Klutke, "The promise of tension-free vaginal tape for female SUI," Contemporary Urol. pp. 59-73, October 2000; and PCT Patent Publication No. WO 00/74633 A2: "Method and Apparatus for Adjusting Flexible Areal Polymer Implants."

Surgical meshes used for the repair of pelvic organ prolapse and treatment of stress urinary incontinence may be woven or knitted mesh fabric materials made from a synthetic polymeric material such as polypropylene. This mesh fabric consists of fibers/strands of polymeric material, typically formed in a width and length that is sufficient to allow the final configuration/pattern to be cut from it. This mesh fabric inherently consists of fibers/strands that cross over one another and frequently form knots. After the mesh fabric is cut to its final configuration, the ends of the fibers/strands can be sharp and prone to fraying and unraveling.

SUMMARY OF THE INVENTION

According to an aspect of the present invention, surgical films for soft tissue repair are provided. The surgical films comprise at least one sheet of non-filamentous material within which pores are formed.

Other aspects of the invention, among others, pertain to methods of using such surgical films and to kits containing such surgical films.

These and other aspects, embodiments and advantages of the present invention will become immediately apparent to those of ordinary skill in the art upon review of the Detailed Description and any claims to follow.

DETAILED DESCRIPTION

A more complete understanding of the present invention is available by reference to the following detailed description of numerous aspects and embodiments of the invention. The detailed description of the invention which follows is intended to illustrate but not limit the invention.

As noted above, in one aspect of the present disclosure, surgical films for soft tissue repair are provided, which comprise at least one sheet of non-filamentous material within which pores are formed (also referred to herein as a porous, non-filamentous sheet).

The surgical films described herein and the one or more sheets forming the films are typically "substantially two-dimensional" in shape. As used herein a "substantially two-dimensional" object is one whose length and width are at least 100 times greater than the thickness of the material forming the object, for example, whose length and width are each at least 100 to 250 to 500 to 1000 or more times the thickness. For example, surgical films may be in the form of ribbons, sheets, and other more complex sheet-like shapes (see, e.g., FIGS. 1-3 and 5 herein, among numerous other possibilities). In certain embodiments, the films will be able to take on a planar configuration, for example, when placed on a planar surface such as a table top. However, substantially two-dimensional objects, including the surgical films of the present disclosure, need not be planar. For example, such objects may curve in space (e.g., as a substantially two-dimensional orange peel curves around the inner portion of the orange, etc.).

Surgical films in accordance with the present disclosure include, for example, a wide variety of films for soft tissue repair, including films for pelvic floor repair, films for renal pelvis repair, male and female urethral slings, vaginal slings, rectal slings, hernia films (e.g., films for inguinal hernia, hiatus hernia, etc.), films for thoracic wall defects, breast support films and various other soft-tissue surgical support devices, including films for cosmetic and reconstructive surgery, among others. Surgical films may be surgically implanted in a variety of subjects, typically vertebrate subjects, more typically mammalian subjects, including human subjects, pets and livestock.

Surgical films in accordance with the present disclosure may comprise one or more substantially two-dimensional sheets of material in which pores are formed. The films of the present disclosure preferably comprise at least one sheet of non-filamentous material within which pores are formed, i.e., a sheet of material that is not formed from one or more filaments.

In certain embodiments, the films of the present disclosure further comprise a filamentous sheet of material, for example, to enhance the attachment and in-growth of cells to the surface or to provide a slip-resistant texture to the material for better handling by a physician. Examples of filamentous sheets include woven sheets and non-woven sheets (including knitted sheets, felt sheets and spunlaid sheets such as spunbonded sheets and meltblown sheets, among others). In certain other embodiments, the films of the present disclosure do not comprise a filamentous sheet of material.

In some embodiments, the pores in the sheet of porous non-filamentous material may be formed concurrently with the formation of the sheet (e.g., by molding). In some embodiments, the pores in the sheet of porous non-filamentous material may be formed subsequent to sheet formation, for example, by a suitable cutting operation (e.g., die cut, laser cut, water-jet cut, etc.) or by a perforation operation. For example, perforations may be formed using sharp protrusions such as needles. The sharp protrusions may be provided, for instance, on the surface of a plate or rotatable drum. Moreover, the sharp protrusions may be heated above the melting point of the film material in certain embodiments to assist with pore formation, among other possibilities.

If desired, one or more of sheets within the films of the disclosure may be heated (e.g., to smooth out edges and other features, etc.), may be stretched (e.g., to reduce the thickness of the film, to elongate pores in the direction of stretching, to strengthen the film in the direction of stretching due to orientation of polymer molecules within the film, etc.), may be compressed, for instance, by undergoing calendaring or another compression process (e.g., to reduce the film's thickness), or may be subjected to a combination of the preceding processes. In some embodiments, one or more sheets within the porous films of the disclosure may be stretched in two or more directions in a variety of angles with respect to one another, including stretching in perpendicular directions and stretching in non-perpendicular directions.

The preceding processes may be performed at various points during the manufacturing process. For example, a sheet of non-filamentous material may be heated, stretched and/or compressed before the sheet is made porous or afterwards. The preceding processes may also be applied to laminated films that contain two or more sheets of material. In some embodiments, heating and/or compression may be performed to bond multiple sheets to one another.

In certain embodiments, porous sheets may be obtained from various commercial sources such as polypropylene films from DelStar Technologies Inc., Middletown, Del., USA.

Surgical films in accordance with the present disclosure may have one or more of the following advantages relative to filamentous meshes, among others: (a) less surface area for bacterial attachment, (b) the elimination of knots and other contact points further reducing the risk of bacterial infection and contamination, (c) the elimination of cut/terminated fibers, which may cause irritation and trauma and which may lead to fibers unraveling at the edge of a given cut shape, (d) increased stability without exhibiting significant stretching, (e) the porosity of a given film can be controlled such as to produce either a relatively constant pore size, shape and/or distribution throughout the area of the film, or a variable pore size, shape and/or distribution throughout the thickness of the film, (f) controlled surface roughness including smoother surfaces for reduced coefficient of friction at placement and rougher surfaces for increased coefficient of friction at placement (e.g., to provide a physician with a surface that is less slippery and provides better grip and handling), (g) ease of manufacture, (h) potential for improved cellular in-growth (e.g., due to controlled surface roughness and/or controlled porosity) and (i) lighter and more flexible tissue repair materials.

As noted above, surgical films in accordance with the present disclosure may be provided in a wide range of shapes and sizes. A few specific embodiments of the present disclosure will now be discussed in conjunction with the drawings.

Figure 1:
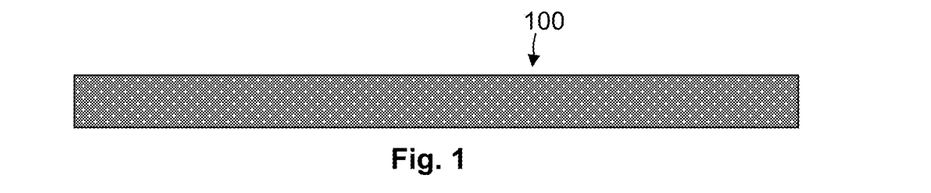
FIG. 1 is a schematic top view of a surgical film, in accordance with an embodiment of the invention.

As one example, there is schematically illustrated in FIG. 1, a surgical film 100, which may be used, for instance, as a urethral sling. The material for the surgical film 100 may comprise a uniform distribution of pores over its surface or through its thickness or a non-uniform distribution of pores over its surface or through its thickness (e.g., the film may be non-uniform in pore shape, non-uniform in pore size, non-uniform in pore density, combinations of the foregoing, etc.). The material for the surgical film 100 may or may not comprise a therapeutic agent. Typical dimensions for such a urethral sling range from 1 to 25 cm (e.g., 1 to 2 to 5 to 10 to 20 to 25 cm) in length and from 1 to 25 cm (e.g., 1 to 2 to 5 to 10 to 20 to 25 cm) in width, among other possibilities.

As previously noted, pelvic floor (pelvic support) disorders involve a dropping down (prolapse) of the bladder, rectum and/or uterus caused by weakness of or injury to the ligaments, connective tissue, and muscles of the pelvis. As with SUI, pelvic floor disorders may be treated by implanting a surgical film in accordance with the present disclosure within the patient's pelvis to support the organ or organs that require support.

Figure 2:
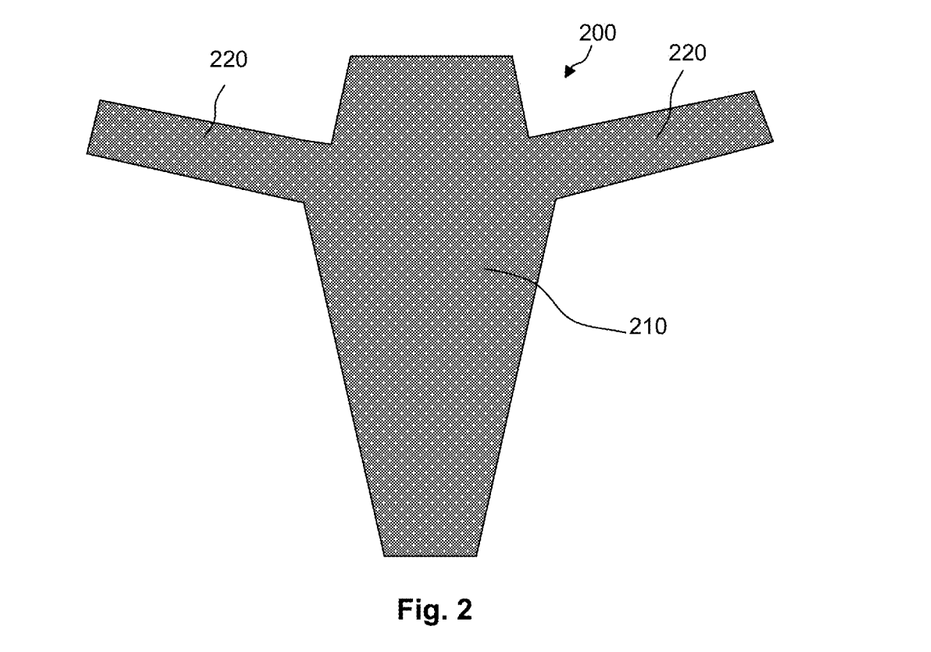
FIG. 2 is a schematic top view of a surgical film which has a central body portion from which a plurality of arms emanate, in accordance with another embodiment of the invention.

In accordance with one embodiment, there is schematically illustrated in FIG. 2 a surgical film 200, for example, a pelvic floor repair film, having a central portion 210 and a plurality of arms 220 that emanate from the central portion 210. As used herein an "arm" is an elongated film component whose length is at least two times greater than its width, typically ranging from 2 to 3 to 4 to 5 to 6 to 8 to 10 or more times the width. (In this regard, surgical sling 100 of FIG. 1 can be thought of as a single-arm device.) As with the film of FIG. 1, the material for the surgical film 200 may comprise a uniform distribution of pores or a non-uniform distribution of pores (e.g., non-uniform in pore shape, non-uniform in pore size, non-uniform in pore density, combinations of the foregoing, etc.).

Figure 3:
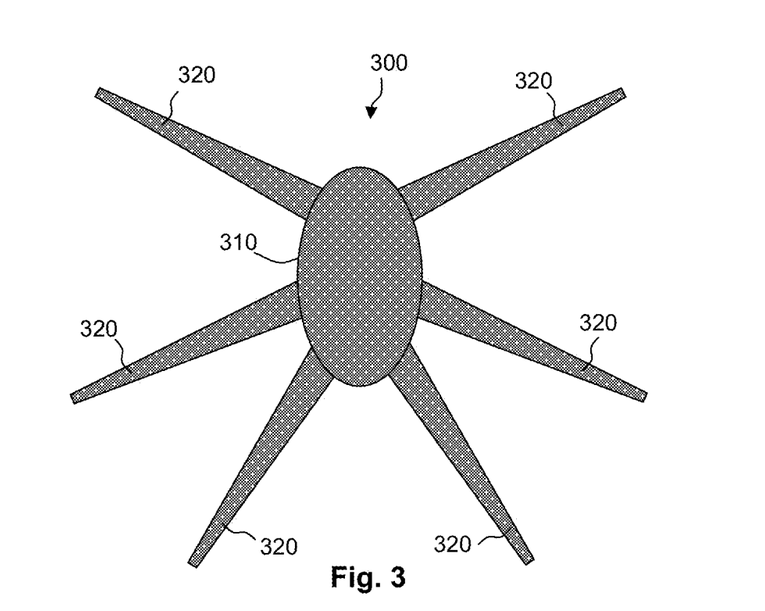
FIG. 3 is a schematic top view of a surgical film which has a central body portion from which a plurality of arms emanate, in accordance with an additional embodiment of the invention.

Although the film of FIG. 2 has two rectangular arms and a polygonal central body portion, other body and arm shapes and other numbers of arms (e.g., 3, 4, 5, 6, 7, 8, etc.) may be used. As one specific variation, FIG. 3 illustrates a film 300 having a non-circular (oval) central body portion 310 and six non-rectangular (trapezoidal) arms 320, among near-limitless other possibilities.

Materials for forming films in accordance with the present disclosure include those formed from various synthetic biostable polymers, various synthetic biodisintegrable polymers, various naturally occurring biostable polymers, various naturally occurring biodisintegrable polymers, as well as various biologics. A combination of biostable and biodisintegrable materials may be employed in certain embodiments. In certain embodiments, covalently crosslinked materials may be employed (e.g., to increase stability, increase strength, etc.).

Examples of synthetic biostable polymers (which can yield permanent implants) may be selected from the following: (a) polyolefin homopolymers and copolymers, including homopolymers and copolymers of C2-C8 alkenes, for example, polyethylene and polypropylene among others, (b) fluoropolymers, including homopolymers and copolymers of C2-C8 alkenes in which one or more hydrogen atoms are substituted with fluorine, for example, polytetrafluoroethylene (PTFE), polyvinylidene fluoride (PVDF), poly(vinylidene fluoride-co-hexafluoropropene) (PVDF-HFP) among others, (c) polyamides such as nylons, among others, (d) polyesters, including, for example, polyethylene terephthalate, among others, (e) polyurethanes such as polyisobutylene based polyurethanes (PIB-PU), among others, (f) polyoxyalkylenes including homopolymers of trioxane (polytrioxane, also known as polyoxymethylene or acetal) and copolymers of trioxane (e.g., copolymers of trioxane and dioxane), (g) styrenic copolymers such as isobutylene-styrene copolymers, including block copolymers comprising one or more polystyrene blocks and one or more polyisobutylene blocks, for instance, poly(styrene-b-isobutylene-b-styrene) (SIBS), among others, (h) as well as various other non-absorbable polymers.

Examples of synthetic biodegradable polymers may be selected, for example, from polyesters and polyanhydrides, among others. Specific biodegradable polymers may be selected from suitable members of the following, among others: (a) polyester homopolymers and copolymers (including polyesters and poly[ester-amides]), such as polyglycolide, polylactide (PLA), including poly-L-lactide, poly-D-lactide, and poly-D,L-lactide, poly(lactide-co-glycolide) (PLG), including poly(L-lactide-co-glycolide), poly(D-lactide-co-glycolide) and poly(D,L-lactide-co-glycolide), poly(beta-hydroxybutyrate), poly-D-gluconate, poly-L-gluconate, poly-D,L-gluconate, poly(epsilon-caprolactone), poly(delta-valerolactone), poly(p-dioxanone), poly(trimethylene carbonate), poly(lactide-co-delta-valerolactone), poly(lactide-co-epsilon-caprolactone), poly(lactide-co-beta-malic acid), poly(lactide-co-trimethylene carbonate), poly(glycolide-co-trimethylene carbonate), poly(beta-hydroxybutyrate-co-beta-hydroxyvalerate), poly[1,3-bis(p-carboxyphenoxy)propane-co-sebacic acid], poly(sebacic acid-co-fumaric acid), and poly(ortho esters) such as those synthesized by copolymerization of various diketene acetals and diols, among others; and (b) polyanhydride homopolymers and copolymers such as poly(adipic anhydride), poly(suberic anhydride), poly(sebacic anhydride), poly(dodecanedioic anhydride), poly(maleic anhydride), poly[1,3-bis(p-carboxyphenoxy)methane anhydride], and poly[alpha, omega-bis(p-carboxyphenoxy)alkane anhydrides] such as poly[1,3-bis(p-carboxyphenoxy)propane anhydride] and poly[1,3-bis(p-carboxyphenoxy)hexane anhydride], among others.

Where copolymers are employed, copolymers with a variety of monomer ratios may be available. For example, where isobutylene-styrene copolymers (e.g., SIBS) are used, the ratio of monomers in these polymers can be selected to obtain mechanical properties such that tissue compatibility is enhanced. For instance, a higher isobutylene content will result in a softer polymer that may be a better match for the durometer of the surrounding tissue. As another example, where PLG is used, a variety of lactide:glycolide molar ratios will find use herein, and the ratio is largely a matter of choice, depending in part on any coadministered adsorbed and/or entrapped species and the rate of degradation desired. For instance, a 50:50 PLG polymer, containing 50% D,L-lactide and 50% glycolide, will provide a faster resorbing copolymer, while 75:25 PLG degrades more slowly, and 85:15 and 90:10, even more slowly, due to the increased lactide component. Degradation rate can also be controlled by such factors as polymer molecular weight and polymer crystallinity. More broadly, where used, PLG copolymers include those having a lactide/glycolide molar ratio ranging, for example, from 10:90 or less to 15:85 to 20:80 to 25:75 to 40:60 to 45:55 to 50:50 to 55:45 to 60:40 to 75:25 to 80:20 to 85:15 to 90:10 or more, and having a molecular weight ranging, for example, from 5,000 or less to 10,000 to 20,000 to 40,000 to 50,000 to 70,000 to 100,000 to 200,00 or more Daltons.

Where a biodegradable polyester is used (e.g., PLA, PLGA, etc.), one or more soft blocks (e.g., polyethylene oxide, polycaprolactone, etc.) may be included with one or more polyester blocks in the polymer to vary hardness, elongation, and degradation rate of the polymer.

Examples of naturally occurring polymers include biostable and biodegradable polymers such as cellulose, biocellulose, and alginates (non crosslinked and ionically crosslinked).

As defined herein, a "biologic material" is a material that comprises one or more extracellular matrix components. Biologic materials for use herein include crosslinked and non-crosslinked allograft (e.g., human cadaveric) materials, as well as crosslinked and non-crosslinked heterograft (e.g., bovine, porcine, equine, etc.) materials. Specific examples of non-crosslinked biologic materials include mammalian non-crosslinked biologic matrix materials, such as human dermis, human fascia lata, fetal bovine dermis and porcine small intestinal submucosa. Specific examples of crosslinked biologic materials include mammalian crosslinked biologic materials such as crosslinked porcine dermis, crosslinked porcine small intestinal submucosa, crosslinked bovine pericardium, and crosslinked horse pericardium. Such materials are typically acellular. Moreover, they are typically predominantly formed of collagen.

The overall thickness of the surgical films of the present disclosure may range, for example, from 25 µm or less to 50 µm to 75 µm to 100 µm to 125 µm 150 µm to 200 µm to 250 µm to 300 µm to 400 µm to 500 µm or more, in certain embodiments, more typically 50 to 300 µm. The overall thickness may be the same over the entire film in some embodiments, whereas in other embodiments the thickness may vary over the lateral surface of the film.

As a specific example, in a surgical film with a central body portion and one or more arms (see, e.g., FIGS. 2 and 3), the film may be compressed (e.g., by calendaring or another process), so as to reduce the thickness of the film in certain areas. As another example, lamination may be used to increase the thickness of the surgical films in certain areas. In this way, a film may be formed in which the arms of the film may be about 200 µm to 300 µm in thickness whereas the central portion of the film may be about 75 µm to 125 µm in thickness, among other possibilities.

Surgical films in accordance with the present disclosure include films having small pores (less than 1 mm) and those having large pores (greater than or equal to 1 mm). Pore shape, size and distribution can vary widely and may be customized for optimal mechanicals and/or tissue response.

In various embodiments, porous sheets within the surgical films of the present disclosure preferably have pore sizes ranging from 10 µm or less to 25 µm to 50 µm to 100 µm to 0.25 mm to 0.5 mm to 1 mm to 2.5 to 5 mm to 10 mm or more in width, more preferably ranging 0.5 mm to 0.75 mm to 1 mm to 2 mm to 3 mm to 4 mm to 5 mm in width. The pore size can be varied prevent or promote tissue in-growth. Pores can extend through the thickness of the film or extend only a portion of the way through the film (e.g., where a porous sheet is laminated to a non-porous sheet).

Figure 4A:
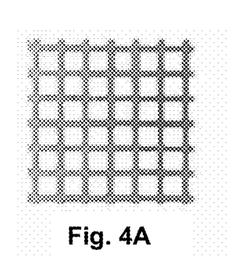
FIGS. 4A-4F are schematic illustrations of pore shapes, in accordance with various embodiments of the invention.
Figure 4B:
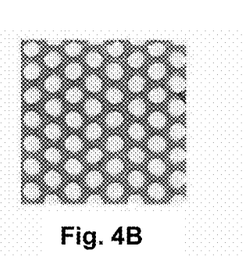
Figure 4C:
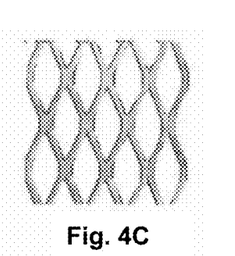
Figure 4D:
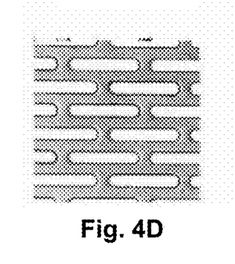
Figure 4E:
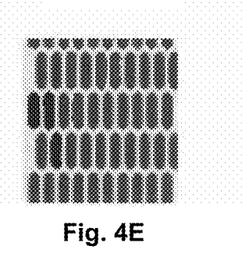
Figure 4F:
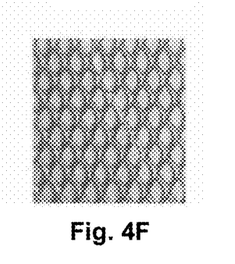

A wide variety of regular and irregular pore shapes may be employed in the films described herein including circular pores, oval pores, regular polygonal pores and elongated polygonal pores, among many others. Pores typically have at least one plane of symmetry, more typically two or more planes of symmetry. Pores typically have an surface aspect ratio (length divided by width) ranging from 1 to 2 to 5 to 7.5 to 10 or more. A few examples of possible pore shapes are illustrated in FIGS. 4A-4F and include square (regular polygonal) shapes (FIG. 4A), circular shapes (FIG. 4B), diamond shapes (FIGS. 4C and 4E), and elongated shapes with rounded ends (FIGS. 4D and 4E). In one specific example, elongated pores having an aspect ratio of about 1.5 (e.g., pores of about 2 mm in width and about 3 mm in length) are provided.

Pore density (pore area divided by total sheet area) can range, for example, from 1% or less to 90% or more within the porous sheets of the present disclosure (e.g., ranging from 1% to 2% to 5% to 10% to 25% to 50% to 75% to 90%).

In certain embodiments, the pore shape, size and density is the same throughout the thickness of the film. In other embodiments the pore shape, size and density may, independently, vary over the thickness of the film. For example, pore size and/or pore density may decrease from an upper surface to a lower surface of the device, may decrease from an upper surface to a central region of the device and then increase from the central region to a bottom surface of the device, and so forth.

The shape, size, density and distribution of the pores may be selected, for instance, to provide suitable mechanical characteristics, to support tissue ingrowth and/or anatomic repair, and so forth. In certain embodiments, the pore shape, size, density and distribution is relatively constant over the entire surface of the film (e.g., the pore size and pore density do not vary by more than 25% over the surface of the film), whereas in other embodiments the pore shape, size and density may, independently, vary over the surface of the film. For example, one or both of the pore size and pore density may vary by 25% or more over the surface of the film, for example, increasing from 25% to 50% to 75% to 100% to 250% to 500% to 1000% or more over the surface of the film.

In one specific example, a surgical film like that of FIG. 1 may be only partially perforated so that one portion of the film surface area is porous and another portion of the film surface area is non-porous. For instance, material near the edges of the film 100 may be solid (non-perforated) and therefore exhibit greater strength relative to the center of the film (e.g., to assist in the attachment of the film to the body).

Surgical films in accordance with the present disclosure may comprise a variety of surface features. For example, depressions such as blind holes and trenches, or protuberances such as ridges, pillars and micro-hooks may be provided at the surfaces of the surgical films. Protuberances may be molded, or they may be generated on a previously formed film surface (e.g., heated needles may be used to elevate micro-hooks from a smooth film surface by dragging the needles for short distance, among other processes). Depressions may likewise be molded or generated (e.g., by calendaring, cutting, etc.) on the film surface.

Protuberances such as micro-hooks may be provided on the surface to increase tissue adhesion (and, in some embodiments, eliminate the need of suture fixations).

In certain embodiments, micro-grooves may be provided on the film surface to promote cell/tissue attachment. Such surface depressions may also act as reservoirs for loading various therapeutic agents.

In embodiments where micro-hooks are provided on one or more portions of the device (e.g., at the ends of the arms of a multi-arm device, etc.), a sleeve may be provided over the micro-hooks, which sleeve can be removed once the device is positioned within the body (e.g., to prevent the micro-hooks from prematurely attaching to tissue before the film is properly positioned).

In various embodiments, the films of the present disclosure may comprise various additional agents (i.e., agents in addition to the polymeric or biologic material that is used to form the film) including therapeutic agents, imaging agents, plasticizers, and fillers, among other agents.

In certain embodiments, the films of the present disclosure comprise one or more antimicrobial agents as therapeutic agents, more preferably, one or more antibiotic agents. Such substances are provided, for example, to reduce the risk of microbial infection upon implantation of the film (including biofouling of the film and infection in surrounding tissue), among other purposes.

Antibiotic agents may be selected, for example, from one or more of the following: the penicillins (e.g., penicillin G, methicillin, oxacillin, ampicillin, amoxicillin, ticarcillin, etc.), the cephalosporins (e.g., cephalothin, cefazolin, cefoxitin, cefotaxime, cefaclor, cefoperazone, cefixime, ceftriaxone, cefuroxime, etc.), the carbapenems (e.g., imipenem, metropenem, etc.), the monobactems (e.g., aztreonem, etc.), the carbacephems (e.g., loracarbef, etc.), the glycopeptides (e.g., vancomycin, teichoplanin, etc.), bacitracin, polymyxins, colistins, fluoroquinolones (e.g., norfloxacin, lomefloxacin, fleroxacin, ciprofloxacin, enoxacin, trovafloxacin, gatifloxacin, etc.), sulfonamides (e.g., sulfamethoxazole, sulfanilamide, etc.), diaminopyrimidines (e.g., trimethoprim, etc.), rifampin, aminoglycosides (e.g., streptomycin, neomycin, netilmicin, tobramycin, gentamicin, amikacin, etc.), tetracyclines (e.g., tetracycline, doxycycline, demeclocycline, minocycline, etc.), spectinomycin, macrolides (e.g., erythromycin, azithromycin, clarithromycin, dirithromycin, troleandomycin, etc.), and oxazolidinones (e.g., linezolid, etc.), among others, as well as pharmaceutically acceptable salts, esters and other derivatives of the same.

In some embodiments, any two of the above antibiotics may be employed in ratios (wt:wt) ranging from 5:95 or less to 10:90 to 15:85 to 20:80 to 25:75 to 30:70 to 40:60 to 50:50 to 60:40 to 70:30 to 75:25 to 80:20 to 85:15 to 90:10 to 95:5 or more. One antibiotic combination that has proven extremely effective against a broad spectrum of skin-borne pathogens is minocycline and rifampin. Other common antibiotics (e.g., gentamicin, tetracyclines, etc.) can also be used, either alone or in combination to address such pathogens.

Other examples of therapeutic agents that may be supplied include the following, among many others: (a) anti-inflammatory agents (e.g., for purposes of reducing macrophage levels, resulting in less muscle regeneration and re-growth) including corticosteroids such as hydrocortisone and prednisolone, and non-steroidal anti-inflammatory drugs (NSAIDS) such as aspirin, ibuprofen, and naproxen; (b) narcotic and non-narcotic analgesics and local anesthetic agents (e.g., for purposes of minimizing pain); (c) growth factors such as epidermal growth factor and transforming growth factor-α (e.g., for purposes of stimulate the healing process and or promoting growth of collagenous tissue); and (d) combinations of the foregoing.

Therapeutic agents may be associated with the films in various ways, including the following, among others: (a) loaded in the interior (bulk) of one or more sheets within the film, (b) bound to the surface of one or more sheets within the film by covalent interactions and/or non-covalent interactions (e.g., interactions such as van der Waals forces, hydrophobic interactions and/or electrostatic interactions, for instance, charge-charge interactions, charge-dipole interactions, and dipole-dipole interactions, including hydrogen bonding), (c) applied as a coating (biostable or biodegradable) that at least partially surrounds one or more sheets within the film, and (d) combinations of the forgoing.

In various embodiments, at least one therapeutic agent is provided within a polymeric matrix. In some of these embodiments, the polymeric matrix corresponds to a bulk sheet material within the film. In others of these embodiments, the polymeric matrix corresponds to a coating on a sheet within the film. In various embodiments, the polymeric matrix (e.g., bulk or coating material) contains 1 wt % or more of one or more therapeutic agents (e.g., from 1 wt % to 2 wt % to 5 wt % to 10 wt % to 25 wt % to 40 wt % to 50 wt % to 60 wt % to 70 wt % to 80 wt % to 90 wt % to 95 wt % to 98 wt % to 99 wt % or more).

Films in accordance with the present disclosure preferably contain from 0.1 to 200 g of one or more therapeutic agents per $m^2$ of film area (e.g., from 0.1 to 0.2 to 0.5 to 1 to 2 to 5 to 10 to 25 to 50 to 100 to 200 $g/m^2$). For example, a film that is 5 cm wide and 20 cm long has a film area of 100 $cm^2$ or 0.01 $m^2$. If such a film were to be loaded with a total of 0.25 g of one or more therapeutic agents, that film would have an antibiotic loading of 0.25 g÷0.01 $m^2$=25 $g/m^2$.

As noted above, coatings in accordance with the present disclosure may contain one or more polymers, which may be selected, for example, from synthetic biostable or biodisintegrable polymers, naturally occurring biostable or biodisintegrable polymers, and biologics, specific examples of which are set forth above, as well as additional polymers such as poly(vinyl alcohol) (PVA) and ethylene vinyl acetate (EVA) copolymers, among others. Coatings may also contain one or more non-polymeric matrix materials, such as trehalose, fatty acids, triglycerides and iopromide, among others.

Biodisintegrable coatings may have an added benefit, for example, of ensuring essentially 100% release of any therapeutic agent therein. Biostable coatings, on the other hand, may have an added benefit, for example, of protecting an underlying film material (e.g., from oxidation, etc.).

Typical therapeutic-to-polymer ratios (wt:wt) within the polymeric matrices (e.g., coatings, bulk, etc.) range from 1:95 or less to 2:98 to 5:95 to 10:90 to 15:85 to 20:80 to 25:75 to 30:70 to 40:60 to 50:50 to 60:40 to 70:30 to 75:25 or more.

The amount and type of polymer that is selected will control the dose and duration of release.

Typical coating thicknesses range from 1 micrometer (micron) or less to 15 microns or more (e.g., from 1 to 2 to 5 to 7.5 to 10 to 12.5 to 15 microns in thickness), among other values.

As noted above, in many embodiments, sheets forming the films described herein are not coated. For example, a sheet may be formed from a mixture comprising polymer(s), therapeutic agent(s), any other optional additional materials, solvents (if needed), and so forth. The resulting therapeutic-agent-containing film may then serve both a structural (e.g., load bearing) function and a drug release function. Alternatively, the resulting therapeutic-agent-containing sheet may be combined (e.g., laminated) with one or more structural sheets that do not contain a therapeutic agent and discussed below. Therapeutic-agent-containing sheets and structural sheets may be formed using one or more biostable or biodegradable materials, selected, for example, from those set forth above.

Examples of plasticizers that may be used as additional agents can be selected from one or more of the following organic plasticizers, among others: citrate esters such as tributyl, triethyl, triacetyl, acetyl triethyl, and acetyl tributyl citrate (ATBC), dioxane, phthalate derivatives such as dimethyl, diethyl and dibutyl phthalate, glycerol, glycols such as polypropylene, propylene, polyethylene and ethylene glycol, surfactants such as sodium dodecyl sulfate and polyoxymethylene (20) sorbitan and polyoxyethylene (20) sorbitan monooleate. Such plasticizers may be provided for better handling and a more robust polymeric matrix (e.g., bulk filament, coating, etc.).

Examples of imaging agents include (a) contrast agents for use in connection with x-ray fluoroscopy, including metals, metal salts and oxides (particularly bismuth salts and oxides), and iodinated compounds, among others, (b) contrast agents for use in conjunction with ultrasound imaging, including organic and inorganic echogenic particles (i.e., particles that result in an increase in the reflected ultrasonic energy) or organic and inorganic echolucent particles (i.e., particles that result in a decrease in the reflected ultrasonic energy), and (c) contrast agents for use in conjunction with magnetic resonance imaging (MRI), including contrast agents that contain elements with relatively large magnetic moment such as Gd(III), Mn(II), Fe(III) and compounds (including chelates) containing the same, such as gadolinium ion chelated with diethylenetriaminepentaacetic acid.

In certain embodiments, the surgical film is rendered electrically conductive (e.g., in its entirety or certain portions thereof), allowing electrical characteristics of the film (e.g., resistance, capacitance, inductance, etc.) to be measured, for instance, across a length of the film or through a thickness of the film. For example, the impedance (e.g., simple DC resistance, complex AC impedance, etc.) for the film may be measured during or after implantation of the film. Such electrical characteristics may provide health care professionals with information regarding mesh breakage and mesh shrinkage, among other information.

For example, an electrically conductive agent (e.g., a conductive metal, conductive polymer, etc.) can be provided on or within the surgical film, making the film electrically conductive. In this regard, the surgical film may be coated or impregnated with a conductive agent, or a second sheet with conductive characteristics may be laminated with a first sheet (which may or may not have conductive characteristics), for example, uniformly over the first or only in selected areas of the first sheet to provide electrical monitoring capabilities.

The film may be provided with electrical contact points for measurement via external electrical measurement equipment, or the film may be provided with one or more components to assist with data measurement including, for example, components for data measurement, data storage, data retrieval (e.g., by direct electromechanical contact with the film or by remote methods, such as radiofrequency communication), and power generation (e.g., via a battery or via components for inductively coupling power from an external source), among others, allowing medical personnel to monitor the film post-implantation.

As previously indicated, surgical films in accordance with the present disclosure may comprise one or more laminated regions, in which 2, 3, 4, 5 or more sheets are laminated to form a multi-layer structure. The use of two or more laminated sheets allows, for example, for the creation of different properties at the top and bottom of the film. The use of three or more laminated sheets allows, for example, for one to change properties (e.g., porosity, composition, etc.) as a function of depth.

In certain embodiments, as previously indicated, the entire film may be formed from multiple laminated sheets. In other embodiments, one or more portions of the device (but not the entire device) may be formed from multiple laminated sheets.

Each laminated sheet may independently have a thickness ranging, for example, from 10 µm to 15 µm to 20 µm to 25 µm 50 µm to 75 µm to 100 µm to 150 µm to 200 µm to 250 µm to 300 µm to 400 µm to 500 µm or more.

Each laminated sheet may, independently, be non-porous or may have a pore size ranging, for example, from pore sizes ranging from 10 µm or less to 25 µm to 50 µm to 100 µm to 0.25 mm to 0.5 mm to 1 mm to 2.5 to 5 mm to 10 mm or more in diameter. In this way, all or a portion of at least one surface (e.g., top and/or bottom surface) may be rendered porous. Moreover, one or more portions of a given device surface may be rendered porous. For instance, in the case of a surgical film having a body portion and one or more arms, all or part of the body portion surface may be made porous, all or part of the arm(s) surface may be made porous, and so forth.

In certain embodiments, two porous sheets may be laminated in which the average pore size, the average pore density, or both, vary by at least 25% from sheet to sheet, for example, increasing from 25% to 50% to 75% to 100% to 250% to 500% to 1000% or more from sheet to sheet.

Each laminated sheet may, independently, be smooth or may have surface texturing on one or both surfaces. In this way, all or a portion of at least one surface (e.g., top and/or bottom surface) may be textured. Moreover, one or more portions of a given device surface may be textured. For instance, in the case of a surgical film having a body portion and one or more arms, all or part of the body portion surface may be textured, all or part of the arm(s) surface may be textured, and so forth.

Each laminated sheet may, independently, be formed from a synthetic biostable polymer, a synthetic biodisintegrable polymer, a natural biostable polymer, a natural biodisintegrable polymer, or a biologic material. In this way, all or a portion of at least one surface (e.g., top and/or bottom surface) may be rendered biodisintegrable. Moreover, one or more portions of a given device surface may be rendered biodisintegrable. For instance, in the case of a surgical film having a body portion and one or more arms, all or part of the body portion surface may be rendered biodisintegrable, all or part of the arm(s) surface may be rendered biodisintegrable, and so forth. For example, a biodisintegrable laminated sheet (which may or may not contain a therapeutic agent) can be placed over a biostable porous laminated sheet in order to temporarily obscure the porosity of the porous laminated sheet. As another example, a therapeutic-agent-containing biodisintegrable laminated sheet may be placed over a biostable laminated sheet in order to promote drug release. As another example, a series of therapeutic-agent containing biodisintegrable laminated sheets, each having differing biodisintegrability characteristics, may provide for complex therapeutic agent release characteristics.

Each laminated sheet may, independently, contain no additional agent or may contain one, two or more additional agents (e.g., therapeutic agents, imaging agents, conductive agents, plasticizers, fillers, etc.). This allows one to provide additional agents in some parts of the device but not in others. For instance, an additional agent may be provided on one or both surfaces of the film, a gradient of an additional agent may be provided as a function of depth, an additional agent may be provided on portions of a surface but not others (e.g., on the body of a device but not on the arms, on the arms of a device but not on the body, etc.), and so forth.

Figure 5:
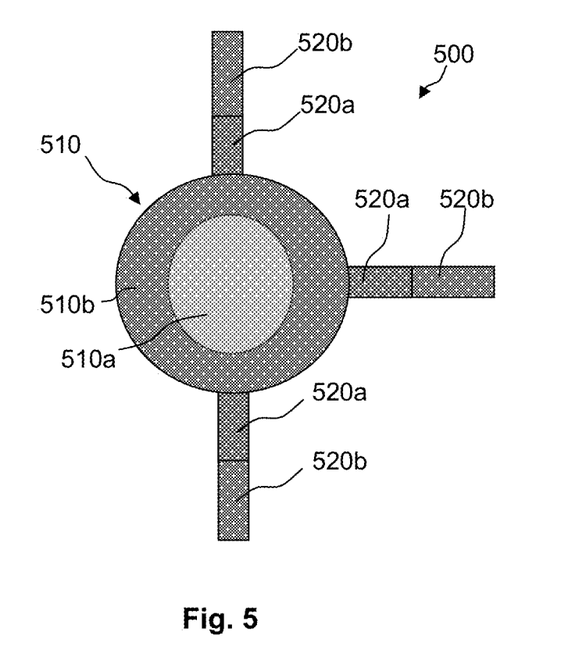
FIG. 5 is a schematic top view of a surgical film which has a central body portion from which a plurality of arms emanate, in accordance with yet another embodiment of the invention.

Turning now to FIG. 5, there is schematically illustrated a mesh 500, for example, a pelvic floor repair film, having a body portion 510 and a plurality of arms that emanate from the body portion 510. The central body portion 510 includes an inner body portion 510a and outer body portion 510b. In certain embodiments, the properties of the inner body portion 510a and outer body portion 510b are varied (a) by providing a laminated sheet in only the inner body portion 510a, (b) by providing a laminated sheet in only the outer body portion 510b, or (c) by providing differing laminated sheets in the inner body portion 510a and outer body portion 510b, respectively. Each of the three arms of the film has an inner arm portion 520a and an outer arm portion 520b. In certain embodiments, the properties of the inner arm portion 520a and outer arm portion 520b are varied (a) by providing a laminated sheet in only the inner arm portion 520a, (b) by providing a laminated sheet in only the outer arm portion 520b, or (c) by differing laminated sheets in the inner arm portion 520a and outer arm portion 520b, respectively.

In other aspects of the present disclosure, a medical kit is provided. The medical kit comprising any combination of two or more of the following items: (a) a sterile surgical film in accordance with the present disclosure, (b) suitable packaging material and (f) printed material with one or more of the following: (i) storage information and (ii) instructions regarding how to implant the surgical film in a subject.

Various aspects of the disclosure relating to the above are enumerated in the following paragraphs:

Aspect 1. A surgical film for soft tissue repair, said surgical film comprising a first sheet of non-filamentous material within which pores are formed.

Aspect 2. The surgical film of aspect 1, wherein said pores range from 0.1 mm to 5 mm in width.

Aspect 3. The surgical film of any of aspects 1-2, wherein the pore size, pore density, or both varies by more than 50% over the surface of the first sheet.

Aspect 4. The surgical film of any of aspects 1-3, wherein said film further comprises a second sheet of filamentous or non-filamentous material that is laminated to the first sheet of non-filamentous material.

Aspect 5. The surgical film of aspect 4, wherein pores are not formed within the second sheet of filamentous or non-filamentous material.

Aspect 6. The surgical film of aspect 4, wherein pores are formed within the second sheet of filamentous or non-filamentous material.

Aspect 7. The surgical film of aspect 6, wherein the pore size or pore density of the first sheet of non-filamentous material is at least 50% greater than that of the second sheet of filamentous or non-filamentous material.

Aspect 8. The surgical film of aspect 4, wherein the first sheet of non-filamentous material and the second sheet of filamentous or non-filamentous material are coextensive throughout the surgical film.

Aspect 9. The surgical film of aspect 4, wherein the first sheet of non-filamentous material is only partially covered by the second sheet of filamentous or non-filamentous material.

Aspect 10. The surgical film of aspect 4, wherein the first sheet of non-filamentous material is biostable and the second sheet of filamentous or non-filamentous material is biodisintegrable.

Aspect 11. The surgical film of aspect 4, wherein the first sheet of non-filamentous material comprises a therapeutic agent and the second sheet of filamentous or non-filamentous material does not comprise a therapeutic agent.

Aspect 12. The surgical film of aspect 4, wherein said film further comprises a third sheet of filamentous or non-filamentous material laminated to the first sheet of non-filamentous material, the second sheet of filamentous or non-filamentous material, or both.

Aspect 13. The surgical film of any of aspects 1-12, where the film comprises surface texturing on one or both surfaces.

Aspect 14. The surgical film of aspect 13, where the film comprises surface texturing on one surface but not on the opposing surface.

Aspect 15. The surgical film of any of aspects 1-14, where the first sheet of non-filamentous material comprises microhooks that increase tissue adhesion.

Aspect 16. The surgical film of any of aspects 1-15, wherein the first sheet of non-filamentous material comprises a therapeutic agent, an imaging agent, or both.

Aspect 17. The surgical film of any of aspects 1-16, comprising one or more components for measuring the electrical properties of the film along its surface or through its thickness.

Aspect 18. The surgical film of any of aspects 1-17, wherein the surgical film is a pelvic floor repair film.

Aspect 19. The surgical film of aspect 18, wherein the surgical film comprises a body and two or more arms extending from the body.

Aspect 20. The surgical film of any of aspects 1-19, wherein the film is sterile and is disposed in a package that maintains the sterility of the film.

Aspect 21. A surgical method comprising implanting the film of any of aspects 1-20 into a subject.

Although various embodiments are specifically illustrated and described herein, it will be appreciated that modifications and variations of the present invention are covered by the above teachings and are within the purview of any appended claims without departing from the spirit and intended scope of the invention.

The invention claimed is:

1. A surgical film for soft tissue repair, the surgical film comprising:
   a multi-layer structure having a plurality of laminated sheets, the plurality of laminated sheets including:
   a first sheet of non-filamentous material defining pores;
   a second sheet of filamentous material laminated to the first sheet, the second sheet defining pores; and
   a third sheet of filamentous or non-filamentous material laminated to the first sheet or to the second sheet,
   the surgical film including at least one calendared portion and at least one non-calendared portion, the at least one calendared portion being compressed such that a thickness of the at least one calendared portion is less than a thickness of the at least one non-calendared portion.

2. The surgical film of claim 1, wherein the pores of the first sheet or the second sheet range from 0.1 mm to 5 mm in width.

3. The surgical film of claim 1, wherein the first sheet is laminated to the second sheet such that an average pore size or average pore density varies by at least 25% from the first sheet to the second sheet.

4. The surgical film of claim 1, wherein the second sheet includes a biostable polymer.

5. The surgical film of claim 1, wherein the pores of the second sheet have a different pore size than the pores of the first sheet.

6. The surgical film of claim 1, wherein an average pore size or average pore density of the first sheet of non-filamentous material is at least 50% greater than that of the second sheet of filamentous material.

7. The surgical film of claim 1, wherein the first sheet and the second sheet are coextensive throughout the surgical film.

8. The surgical film of claim 1, wherein the first sheet is only partially covered by the second sheet.

9. The surgical film of claim 1, wherein the first sheet is biostable and the second sheet is biodisintegrable.

10. The surgical film of claim 1, wherein the first sheet comprises a therapeutic agent and the second sheet does not comprise a therapeutic agent.

11. The surgical film of claim 1, where the surgical film comprises surface texturing on only one of a top surface and bottom surface of the multi-layer structure.

12. The surgical film of claim 1, where the first sheet comprises micro-hooks that increase tissue adhesion.

13. The surgical film of claim 1, wherein the first sheet comprises a therapeutic agent, an imaging agent, or both.

14. The surgical film of claim 1, further comprising one or more components for measuring electrical properties of the surgical film.

15. The surgical film of claim 1, wherein the first sheet contains an agent.

16. The surgical film of claim 1, wherein the surgical film includes a body and two or more arms extending from the body.

17. The surgical film of claim 1, wherein the second sheet is a biostable porous laminated sheet, and the third sheet is a biodisintegrable laminated sheet devoid of pores, the third sheet being coupled to the second sheet such that the pores on the second sheet are temporarily obscured by the biodisintegrable laminated sheet.

* * * * *